United States Patent [19]

Young

[11] 4,053,825
[45] Oct. 11, 1977

[54] IONIZATION CHAMBER TYPE GAS LEAK DETECTOR OPERATING IN THE HIGH VOLTAGE AVALANCHE REGION

[75] Inventor: James R. Young, Rexford, N.Y.

[73] Assignee: General Electric Company, Schenectady, N.Y.

[21] Appl. No.: 490,586

[22] Filed: July 22, 1974

[51] Int. Cl.² ............................................. G01N 27/66
[52] U.S. Cl. ........................................ 324/33; 324/36
[58] Field of Search ...................... 324/33, 36, 65 R; 23/254 E; 73/23

[56] References Cited

U.S. PATENT DOCUMENTS

| 2,740,894 | 4/1956 | Deisler, Jr. et al. | 324/33 |
| 3,009,096 | 11/1961 | Vanderschmidt | 324/33 |
| 3,009,098 | 11/1961 | Simons, Jr. | 324/33 |
| 3,071,704 | 1/1963 | Reich | 324/33 |
| 3,361,907 | 1/1968 | Gregory | 324/33 |

FOREIGN PATENT DOCUMENTS

| 810,062 | 3/1959 | United Kingdom | 324/33 |

OTHER PUBLICATIONS

Weast, R. C., (editor), "Handbook of Chem. & Phys.," CRC Press, 1974-1975, 55th edition, pp. B4-B6.
Brown, S. C., "Basic Data of Plasma Physics," M.I.T. Press, 1959, pp. 122-131.
Weissler et al., "Negative Corona in Freon-Air Mixtures" and Positive Corona in Freon-Air Mixtures, Phys. Rev., vol. 72, 1947, pp. 289-297.

Primary Examiner—John K. Corbin
Attorney, Agent, or Firm—Jack E. Haken; Joseph T. Cohen; Jerome C. Squillaro

[57] ABSTRACT

A lower power consumption gas leak detector device includes an ionization chamber with a radioactive source and pointed electrode in close proximity thereto supported within the ionization chamber. The pointed electrode provides a region of high electric field with a lower applied voltage so that the gas leak detector provides a significantly larger current signal for a particular gas leak rate with the device operating in the high voltage avalanche region than if the device was operating in the saturated current region of the current versus applied voltage characteristics of the device.

4 Claims, 6 Drawing Figures

IONIZATION CHAMBER TYPE GAS LEAK DETECTOR OPERATING IN THE HIGH VOLTAGE AVALANCHE REGION

My invention relates to a gas leak detector device of the ionization chamber type, and in particular, to a portable gas leak detector device having low power consumption and sufficient sensitivity for many leak testing applications.

Gas leak detector devices have many applications such as for the safety of personnel in a potentially unhealthy gaseous environment and in the testing of various apparatus requiring a gas for operation thereof, as two typical examples. The discussion herein will be limited to the latter type application, and in particular, for the testing of refrigerant devices such as air conditioners and refrigerators to detect leaks of the heat exchanging gas therein at various connections. The refrigerant gas typically is a halogen type gas such as the trademarked FREON (fluorinated hydrocarbon). The gas leak detector is especially useful as a portable device so that it can be utilized by a serviceman when checking the operation of remotely located refrigerator units such as an automobile air conditioner or household refrigerator which are subject to leaks of the refrigerant gas. This portable type leak detector desirably is a device which requires very little power so that it can operate for long periods of time, preferably on inexpensive discardable batteries, and has sufficient sensitivity for the particular leak testing application.

Conventional halogen leak detectors are sufficiently sensitive for detecting small leaks (in the order of $10^{-5}$ standard cc per second) but require a considerable amount of electrical power (approximately 1 watt) for heating a sensor element utilized therein. As a result of such relatively large power consumption, the leak detector cannot operate on inexpensive discardable batteries, or if it can, the operation is for only short periods of time before the batteries are expended.

Therefore, one of the principal objects of my invention is to provide an improved gas leak detector device requiring very little power for operation thereof.

Another object of my invention is to provide the gas leak detector device with sufficient sensitivity for many gas leak testing applications.

A further object of my invention is to provide a gas leak detector device having a long operating life and a method of operation thereof.

Briefly stated, and in accordance with the objects of my invention, I provide a gas leak detector device which utilizes an ionization chamber operating in the high voltage avalanche (electron multiplication) region of the current versus voltage characteristics of the device. A radioactive alpha particle source attached to a first electrode is supported within the ionization chamber opposite, and in close proximity, to a pointed second electrode. The pointed electrode provides a region of high electric field with a lower voltage applied across the two electrodes than if a nonpointed electrode was utilized. The alpha particles ejected into the region between the two electrodes produce ionization of molecules in the gaseous environment being tested, resulting in free electrons and positive ions. Application of a d.c. voltage across the electrodes results in an electric field that develops current versus voltage characteristics significantly different for air and the particular gas being tested for leaks thereof. In the current saturated region of the current versus voltage characteristics, between 100 and 1500 volts for an electrode spacing of approximately 3 millimeters, an electric current change is readily detected when the particular gas is leaking into air (leaking from a connection or other discontinuity in the refrigerator device or other gas utilizing apparatus being examined). However, in the high voltage avalanche region, i.e., at applied voltages between 2000 and 2500 volts, the electric current change is significantly greater for the same rate of gas leak into air and thus my gas detector device is significantly more sensitive when operating in the high voltage avalanche region than in the current saturated region. The power consumption of my gas leak detector device is less than one watt and can be as low as approximately 200 milliwatts with proper choice of the read-out means. The sensitivity of the device is sufficient to easily detect leaks of fluorinated hydrocarbons (FREON) or sulfur hexafluoride of $10^{-5}$ standard cc per second. The lower power consumption of the device permits the use of a simple battery-operated high voltage d.c. power supply utilizing inexpensive discardable batteries. A simple electronic circuit may be utilized for converting the nanoampere current signal produced in the ionization chamber to a voltage signal that is detected or measured by a suitable read-out device used for indicating the presence and, or, magnitude of the gas leak detected by my device.

The features of my invention which I desire to protect herein are pointed out with particularity in the appended claims. The invention itself, however, both as to its organization and method of operation together with further objects and advantages thereof may best be understood by reference to the following description taken in connection with the accompanying drawing wherein:

Figure 1:
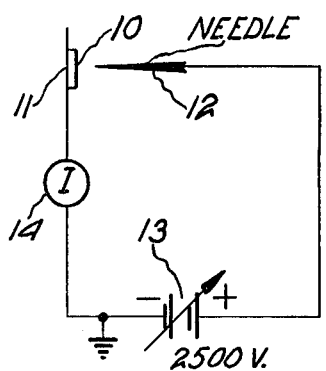
FIG. 1 is a schematic representation of the gas leak detector device in accordance with my invention.

Referring now in particular to FIG. 1, there is shown a schematic diagram of my gas leak detector device which basically consists of (1) an ionization chamber including therein an alpha particle radiation source 10 that is attached to a surface of a first electrode 11, and a pointed second electrode 12 in close proximity to the radiation source, (2) low power, high voltage d.c. power supply 13 connected across electrodes 11 and 12, and (3) a suitable current signal processing circuit and read-out means designated as a whole by numeral 14. The read-out means portion of 14 provides a visual or audible indication of the existence of a gas leak detected by my gas leak detector device. By definition, an ionization chamber is a device which measures, or from which can be measured, the amount of ionization created by charged particles passing through the gas in the chamber. The housing of the ionization chamber in which radiation source 10 and pointed electrode 12 are supported in closely spaced relationship is open to the ambient atmosphere so that alpha particles ejected from source 10 into the region between electrodes 11 and 12 produce ionization of gas molecules in the chamber along the alpha particle ejection paths. This ionization results in free electrons and positive ions being formed primarily in and near the inter-electrode region. Upon the application of a voltage across electrodes 11 and 12 as provided by power supply 13, an electric field is formed between the two electrodes, and the current signal in the circuit formed by elements 11-13 is processed by a suitable current sensing and control circuit including the read-out means included in 14. The purpose of the pointed electrode 12 is to provide a region of high electric field between the radiation source 10 attached to electrode 11 and electrode 12 with a relatively lower applied voltage than if two parallel plate electrodes were utilized. Power supply 13 may be a conventional battery-operated high voltage d.c. supply consisting of one or more discardable, inexpensive batteries, a transistorized relaxation oscillator, step-up transformer and rectifier circuit.

Figure 2:
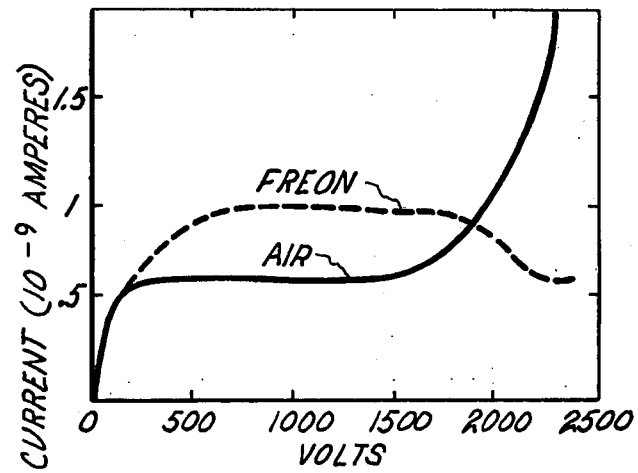
FIG. 2 is a graphical representation of the operation of my device in terms of the current versus applied voltage characteristics in an atmosphere of almost 100% FREON gas.

Typical current versus (applied) voltage characteristics of my leak detector device are illustrated in FIG. 2. These characteristics are for a particular radiation source 10, pointed electrode 12, and ionization chamber to be described hereinafter and thus somewhat different characteristics would be obtained for different radiation sources, pointed electrodes, different sized chamber or different inter-electrode spacings. It can be seen that these characteristics are significantly different for air alone as represented by the solid line curve and for almost 100% fluorinated hydrocarbon gas (identified by the trademark FREON 12 and having the chemical composition of $CCL_2F_2$) as represented by the dashed line curve. The significant difference in these current versus voltage characteristics is the phenemenon which provides my gas leak detector device with the desirable characteristics to be described hereinafter.

The current-voltage characteristics may conveniently be divided into three regions, namely, a low voltage region in the range up to approximately 100 volts, a saturated current region in the range between 100 and approximately 1800 volts and a high voltage avalanche or electron multiplication region above 1800 volts. In the low voltage region, the current increases almost linearly with applied voltage and then saturates for voltages between 100 and 200 volts. The saturated current region is the normal operating region of conventional ionization chambers. In this region, the electric field is sufficient to enable most of the free electrons, negative ions and positive ions to be collected before recombination occurs. As the applied voltage is increased above approximately 1800 volts, some of the free electrons are accelerated to energies sufficiently high to produce additional ionization of the gas which in turn produces an increased current thereby defining the higher voltage region as the electron multiplication or avalanche region. Finally, as the applied voltage is increased still further, beyond approximately 2500 volts, a gas discharge or spark discharge occurs thereby producing a very high current.

The dashed line curve in FIG. 2 represents a concentration of FREON 12 gas approaching 100%. In the low voltage region, the air and FREON curves are substantially identical. In the saturated current region, the current increases in the presence of FREON to a value approximately twice that of an atmosphere of air alone. In the avalanche region, the current decreases in the presence of 100% FREON to a value lower than for air alone by a factor as great as 10 or more and it is this large difference in current which enables my ionization chamber to detect small concentrations of FREON and other gases in air. Both the current saturated region and avalanche region may be used to detect FREON in air, however, the avalanche region provides a significantly larger current signal change for a given concentration or leak rate of FREON due to the rapid rise in the current versus voltage curve for air alone. In the current saturated region a FREON gas leak in the order of $2 \times 10^{-3}$ standard cc per second can be detected whereas in the avalanche region the higher sensitivity permits a leak of $10^{-5}$ standard cc per second to be easily detected.

The current-voltage characteristics in FIG. 1 were obtained with the pointed electrode 12 having a potential positive with respect to the radiation source electrode 11. Results similar to that depicted in FIG. 2 are obtained when the pointed electrode is negative except that the current tends to be unstable. The current is also unstable when the pointed electrode is at the highest positive potential utilized, 2800 to 3000 volts. The maximum signal-to-noise ratio occurs when the pointed electrode 12 is positive, a current of approximately $5 \times 10^{-9}$ ampere and an applied voltage of approximately 2300 volts. This maximum signal-to-noise ratio is quite broad and good sensitivity of my gas leak detector device is achieved at currents between 1 and $9 \times 10^{-9}$ ampere and applied voltages between 2100 and 2800 volts. The desired operating current point for my device is established by adjusting the applied voltage to obtain the desired current.

Figure 3:
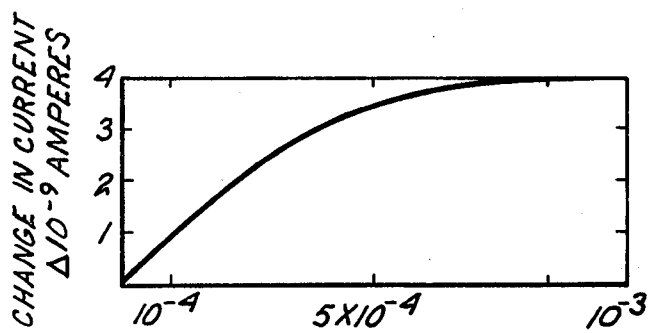
FIG. 3 is a graphical representation of the operation of my device in terms of change in current for various FREON gas leak rates at a fixed applied voltage.

The manner in which the sensitivity of my gas leak detector device varies when operated as a FREON 12 gas leak detector is illustrated graphically in FIG. 3 which depicts the current change versus FREON leak rate when operating an oversized ionization chamber at $5 \times 10^{-9}$ ampere and at approximately 2400 volts. This plot of the current change for various FREON leaks indicates that the ionization chamber is quite sensitive to the presence of the FREON gas in air, but also indicates that the response is not proportional to concentration but tends to saturate at the higher concentrations (or leak rates) of the FREON gas. This saturating characteristic is desirable for leak detection since maximum sensitivity occurs for the lower FREON concentrations and large leaks do not saturate the electronic circuitry that is utilized as an input to the read-out device that indicates the presence, and, or the magnitude of the gas leak, depending on the type of read-out device. The data used in establishing the plot of FIG. 3 was obtained by supporting an alpha particle source 10, first electrode 11 and pointed electrode 12 in an enclosed aluminum container having a volume of 1450 $cm^3$. Various flow rates of FREON and a fixed flow rate of air were introduced into the container, and after equilibrium was established, the resulting known FREON concentrations in the enclosed container were utilized for establishing the curve in FIG. 3. The use of a more typically much smaller sized ionization chamber (that would be used in a practical gas leak detector device for portable application) having diameter and height dimensions each in the order of 0.8 cm obtained data indicating ease in detecting leaks in the order of $1 \times 10^{-5}$ standard cc per second of FREON 12 and the smallest detectable leak was approximately $1 \times 10^{-6}$ standard cc per second.

The data for the curves illustrated in FIGS. 2 and 3 and the above-noted sensitivities of gas detection were obtained with radiation source 10 being a 5 microcurie americium Am 241 alpha particle source that was spot welded to the curved surface of first electrode 11 consisting of a 0.05 inch diameter, ⅜ inch long nickel rod. Pointed electrode 12 was a steel phonograph needle of 0.058 inch diameter, ⅝ inch length and having a tip radius of approximately 0.0025 inch. The radiation source was attached adjacent the free end of the nickel rod along the surface thereof closest to the pointed electrode 12 and spaced 0.080 inch therefrom.

Conventional electronic circuitry is utilized for processing the current signal developed in the circuit including the ionization chamber and d.c. power supply. A typical circuit comprises an operational amplifier functioning as a current-to-voltage amplifier for converting the current signal to a voltage signal, and a pair of output comparators having different preset threshold input levels so that they sense the voltage signal at the operational amplifier output and only one of the comparators provides a voltge output signal when its threshold is exceeded. A small neon or other suitable lamp may be connected in the output of each comparator so that one lamp lights when the ionization chamber current slightly exceeds a normal (no leak) operating point such as $5 \times 10^{-9}$ ampere, and the other lamp lights when the current decreases slightly below this level.

Instead of the comparators and lamps, a voltmeter may be utilized in the output circuit of the operational amplifier for providing a voltage reading that is directly proportional to the magnitude of the ionization chamber current. The voltmeter can then be read and changes in the voltmeter reading can be translated to the current changes that indicate presence of leaks, and the magnitude of the voltage change can be converted to the magnitude of the leak rate. Other suitable readout devices can also be utilized, as desired, it being understood that the device should be small and light in order to render the whole leak detector device readily portable. thus, an audio output in the form of a squealing signal may be used as a warning signal. Also, it should be noted that the read-out device may be one of the largest power consuming elements in my leak detector, and therefore the choice of the read-out device must be carefully considered if minimum power consumption is a criterion for the leak detector application. Component 14 could conceivably merely be an ammeter, although most present day ammeters are not sufficiently sensitive at the low current levels in the nanoampere range occurring in my detector.

My gas leak detector device is also sensitive to gases and vapors other than FREON. As one typical example, sulphur hexafluoride $SF_6$ responds similarly to FREON and my device has approximately the same sensitivity for detecting leaks thereof. In the case of methane $CH_4$ or hydrogen, the signal current increases in the avalanche region which is opposite to that of the response of FREON or $SF_6$. The sensitivity of my device to $CH_4$ or $H_2$ is sufficient to detect such gases at the lower explosive limit in air which is approximately 4% concentration for hydrogen and 5% for methane.

The operating current point of my gas leak detector device increases with the sensor temperature in a manner such that with an operating temperature of 25° C and a voltage of 2400 volts, the current in air is $5 \times 10^{-9}$ ampere and increases to approximately $7 \times 10^{-9}$ ampere at a sensor temperature of 50° C. However, no transient response is observed when the sensor is probing near a body operating at 200° C. My detector is not affected by exposure to large gas leaks. Thus, a $10^{-4}$ standard cc per second leak of FREON gas is detected within 5 to 10 seconds after exposure to approximately 100% concentration of FREON and therefore my detector has the ability to detect small gas leaks within a few seconds after exposure to large leaks. Finally, my detector has a long life, having operated successfully continuously for at least one thousand hours without failure.

Figure 4:
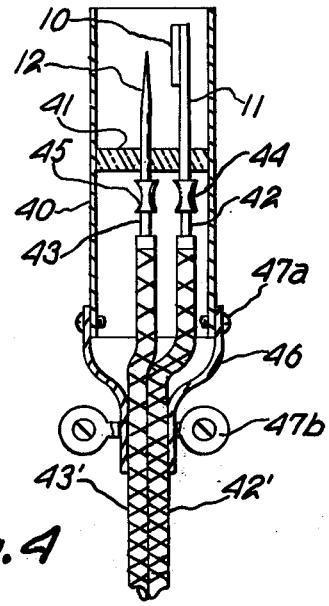
FIG. 4 is a partial sectional view of a first embodiment of the ionization chamber of my device, and electrical conductors connected thereto.
Figure 5:
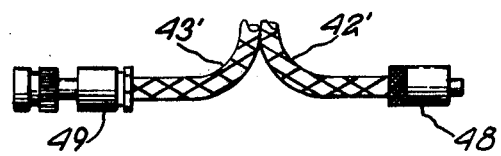
FIG. 5 is a partial sectional view of a second embodiment of the ionization chamber of my device.
Figure 5:
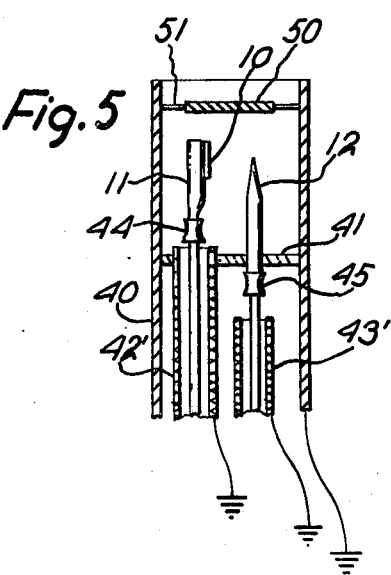
Figure 6:
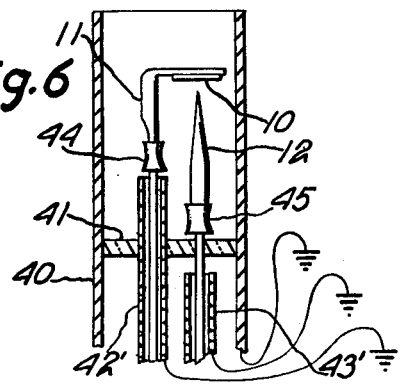
FIG. 6 is a partial sectional view of a third embodiment of the ionization chamber of my device.

FIG. 4 is an enlarged view of a first embodiment of the ionization chamber and interconnecting electrical conductors of my gas leak detector in which the pointed electrode 12 and first electrode 11 with the radiation source 10 with the radiation source 10 attached thereto are in parallel relationship within a housing or chamber 40. The tip of pointed electrode 12 is approximately at the mid-point of radiation source 10 and both these elements are located within chamber 40 but close to a first open end thereof which is used as the probe end that is placed in close contact with a connector, seam or other joint of an apparatus being monitored for possible gas leakage therefrom. Chamber 40 is preferably a hollow open-ended cylindrically shaped metallic housing, i.e., a tubular member open at the first end and fabricated of a sheet metal such as aluminum for providing protection to the electrodes 11 and 12 supported within the chamber. Chamber 40 may typically have an outer diameter of ⅜ inch, inner diameter of 9/32 inch and length of 1¼ inch. The nickel rod forming first electrode 11, and the phonograph needle forming the pointed electrode 12 are rigidly supported within chamber 40 by means of a suitable electrically insulating insert 41 that is pressfit (or otherwise rigidly retained) within chamber 40 and has appropriate holes through which electrodes 11, 12 pass tightly so that the far free ends thereof are retained in fixed spaced apart relationship. Electrode supporting insert 41 may typically be formed of a plastic material such as the trademarked PLEXIGLASS or other suitable electrically insulating material. Insert 41 is spaced approximately 5/16 inch from the first end of tubular body 40 and is of ⅛ to ¼ inch thickness. The ionization chamber therefore is formed within the outer 5/16 inch portion of tubular member 40. The base (i.e., supported) portions of electrodes 11 and 12 are suitably connected to electrical conductors 42 and 43, respectively, wherein such conductors are elements of coaxial cables 42', 43' having the outer shield portions thereof suitably grounded. The connection of electrodes 11 and 12 to conductors 42 and 43 may typically be accomplished by crimping with nickel tube connectors 44 and 45, respectively. The connectors 44 and 45 may be located on the side of insert 41 opposite from the first open end of tubular body 40 as depicted in FIG. 4, or, may be located on the same side thereof as the open end as depicted in FIG. 6, or, the connectors may be located on both sides of insert 41 as depicted in FIG. 5. Coaxial cables 42' and 43' pass through a second end of tubular member 40 which may be closed except for a hole therethrough, or may be open (as illustrated) and enclosed by a suitable cable clamp 46 fastened along the second end of tubular member 40 by means of two screws 47a as a typical example of such connection. Another pair of screws 47b may be utilized at the far end of cable clamp 46 and one of such screws may provide the added function of grounding tubular member 40. The other end of coaxial cable 42' is connected to a small coaxial cable connector 48 which is connected to the input of the electronic current signal processing circuit and read-out device component 14. The other end of the coaxial cable 43' is connected to a high voltage coaxial cable connector 49 which in turn is connected to the positive polarity terminal of the high voltage power supply 13. In operation, the probe portion (housing 40) of my detector is held in one hand of the operator and is placed in the immediate vicinity of the suspected gas leak, and the power supply and electronic circuitry and read-out portion is either held in the other hand or rested on a convenient surface. Any significant change on the read-out device while the probe was moved from a normal ambient atmosphere to the vicinity of the suspected gas leak is an indication that a gas leak does exist, and the magnitude of the change, if obtainable on the particular read-out device employed, may be converted directly to the leak rate.

Referring now to FIG. 5, there is shown a second embodiment of the probe end of my gas leak detector, and in particular, illustrates the electrically shielded insulated portion of coaxial cable 42' extending through and slightly beyond electrode supporting insert 41. The reason for having the grounded (i.e., electrically shielded) portion of coaxial cable 42' extending beyond insert 41 is that the current signal is sensitive to moisture such as water vapor in the air and tends to increase in the presence of moisture. Since this sensitivity to moisture may be detrimental in certain applications, and is caused by moisture condensing along the surface of insert 41 adjacent the first end of tubular body 40, such undesirable characteristic is eliminated by preventing the formation of a moisture-developed low resistance path between the two electrodes along the surface of insert 41. The grounded (electrically shielded) portion of coaxial cable 42' (or 43') passing through insert 41 accomplishes this purpose by forming a guard ring that reduces any leakage current across the surface of insert 41 to substantially zero.

The alpha particles emitted from radiation source 10 are of short range, in the order of a few centimeters, and therefore very few of such particles escape through the first open end of tubular member 40 to the surrounding atmosphere in the FIG. 4 embodiment. However, as a further safeguard for preventing the escape of radiation from the ionization chamber, a suitable radiation shield 50 is utilized in the FIG. 5 embodiment wherein two or more relatively thin wires 51 are utilized for supporting shield 50 within tubular member 40 adjacent the first open end thereof. Shield 50 may typically be a thin disk of lead oriented normal to the longitudinal axis of tubular member 40 so that it absorbs most of any alpha particles directed from source 10 toward the first open end of tubular member 40.

FIG. 6 illustrates a third embodiment of the probe portion of my gas leak detector and is distinguished from the first two embodiments in that the orientation of the pointed electrode 12 is perpendicular to radioactive source 10 as illustrated in the schematic diagram of FIG. 1 and thus is distinguished from the parallel orientation in the FIGS. 4 and 5 embodiments. Spacing between the tip of pointed electrode 12 and the center of radioactive source 10 is the same as the parallel spacing, namely, 0.080 inch. An advantage of the orientation of the radiation source in the FIG. 6 embodiment is that the alpha particles emitted therefrom are directed away from the first open end of tubular member 40 and therefore the radiation source supporting portion of electrode 11 forms an inherent radiation shield to prevent emission of stray alpha particles through the first open end of tubular member 40. With both of connectors 44 and 45 being adjacent the first end of member 40 side of insert 41, it is evident that the electrically shielded insulated portion of coaxial cable 43' could also pass through insert 41, if this was desired. Except for the possible problem of increased current signal in the presence of moisture in the FIG. 4 embodiment, all three embodiments operate in identical manners and have the same current-voltage characteristics while utilizing the same size alpha particle source and electrodes and spacing therebetween.

From the foregoing description, it is apparent that my invention attains the objectives set forth in that it makes available an improved gas leak detector having a lower power consumption so that it may be embodied in a portable device and operate from a power supply including discardable low cost batteries. My detector has sufficient sensitivity for detecting FREON gas leaks occurring from air conditioners, refrigerators and the like, and is also sufficiently sensitive for other gas leak testing applications such as the detection of sulfahexafluoride, hydrogen and methane in air. Finally, my detector has a long operating life and is simple in construction.

Having described my invention, it is believed obvious that modification and variation of my invention is possible in the light of the above teachings. Thus, other alpha particle radiation sources such as radium, may be utilized. Further, the pointed electrode 12 may have other dimensions and spacing from radioactive source 10 and the ionization chamber may have different dimensions than those described hereinabove while still having a satisfactorily operating device. Obviously, electrode 12 need not be a phonograph needle but can be any pointed thin metallic body. It is, therefore, to be understood that changes may be made in the particular embodiment of my invention described which are within the full intended scope of the invention as defined by the following claims.

What I claim as new and desire to secure by Letters Patent of the United States is:

1. A gas leak detector device comprising:
   ionization chamber means open to the ambient for sampling the ambient atmosphere in the region of said ionization chamber means and for producing charged particles means including
   a. a chamber having a first end open to the ambient and a second end,
   b. a first electrode disposed within said chamber and having a first end positioned within said chamber adjacent the first end thereof and having a second end closer to a second end of said chamber and rigidly supported thereat,
   c. a radioactive source attached to said first electrode near the first end thereof, and
   d. a second electrode disposed within said chamber, having a pointed first end positioned in close proximity to said radioactive source for increasing the electric field therebetween upon a high voltage being applied across said first and second electrodes, and having a second end closer to the second end of said chamber and rigidly supported thereat;

said second electrode being oriented perpendicular to said radioactive source so that the pointed first end or said second electrode is the closest portion thereof to the radioactive source, said second electrode and a portion of said first electrode including the second end thereof being oriented parallel to each other and to the longitudinal axis of said chamber; and means connected to said ionization chamber means for operating said ionization chamber means in the high voltage avalanche region of the current versus applied voltage characteristics of the leak detector device which provides a significantly larger current change for a particular rate of a gas leak being detected than if said ionization chamber means was operated in the saturated current region of the current versus applied voltage characteristics so that the leak detector device is substantially more sensitive to smaller leaks of the gas.

2. The gas leak detector device set forth in claim 1 wherein the tip of the pointed first end of said second electrode is spaced approximately centrally of said radioactive source.

3. A method for detecting a leak of a halogen gas from an apparatus comprising the steps of adjusting the output voltage of a battery-operated high voltage d.c. power supply so that an ionization chamber operates in the high voltage avalanche region of the current versus voltage characteristics of the ionization chamber which occurs at higher voltages than for saturated current region operation, positioning an open first end of the ionization chamber in the immediate vicinity of a suspected leak of halogen gas from an apparatus utilizing the gas, viewing a read-out device which is responsive to the significantly larger electrical current change in the circuit of the ionization chamber for a particular leak of the halogen gas as compared to operation of the ionization chamber in the saturated current region so that the gas leak is easily detected, and removing the ionization chamber from the immediate vicinity of the suspected leak, the ionization chamber, power supply and read-out device being small units so that the entire device is readily portable and can be hand-operated.

4. The method set forth in claim 3 wherein the step of viewing the read-out device consists of viewing the device with the ionization chamber located remote from the suspected halogen gas leak and noting the indication thereof, and viewing the device with the ionization chamber positioned in the immediate vicinity of the suspected halogen gas leak and noting the indication thereof and any change in the indication from when the ionization chamber was remotely located, absence of any significant change in the indication of the read-out device being indicative of the absence of a halogen gas leak whereas a significant change in the indication of the read-out device being indicative of the presence of the gas leak.

* * * * *